United States Patent [19]

Garapon et al.

[11] Patent Number: 5,234,476
[45] Date of Patent: Aug. 10, 1993

[54] POLYNITROGEN COMPOUND HAVING TWO TERMINAL CYCLES OF THE IMIDE TYPE, THEIR PREPARATIONS AND USES

[75] Inventors: Jacques Garapon, Lyon; Roger Bregent, Oinville S/Montcient; Rémi Touet, Saint Egreve; Philippe Mulard, St. Pierre de Chandieu; Pierre Schmelzle, St. Julien Molin Molette, all of France

[73] Assignees: Institut Francais du Petrole, Rueil Malmaison; Elf France, Paris, both of France

[21] Appl. No.: 921,799

[22] Filed: Jul. 30, 1992

[30] Foreign Application Priority Data

Jul. 31, 1991 [FR] France .................. 91 09847

[51] Int. Cl.$^5$ .................. C10L 1/22
[52] U.S. Cl. .................. 44/348; 44/347; 548/520; 548/546; 548/547
[58] Field of Search .................. 44/347, 348; 548/520, 548/547, 546

[56] References Cited

U.S. PATENT DOCUMENTS

| | | | |
|---|---|---|---|
| 3,723,460 | 3/1973 | Brannen et al. | 44/63 |
| 3,773,787 | 11/1973 | Dickert et al. | 548/520 |
| 4,233,220 | 11/1980 | Kvita et al. | 548/520 |
| 4,778,900 | 10/1988 | Kohli | 548/547 |
| 4,906,252 | 3/1990 | Gutierrez et al. | 44/347 |

FOREIGN PATENT DOCUMENTS

2152271 10/1970 Fed. Rep. of Germany.
2714403 3/1977 Fed. Rep. of Germany.

OTHER PUBLICATIONS

Chemical Abstracts, vol. 83, No 2, Jul. 14, 1975, Columbus, Ohio, US; Abstract No. 10953R, J. A. Moore et al.; "Polyamine esters, derived from diethyl . . .", p. 4; and Macromolecules 1975, 8(2), 121–7.
Chemical Abstracts, vol. 76, No. 12, Mar. 20, 1972, Columbus, Ohio, U.S.; Abstract No. 60269Y, A. Tai et al.; "Structural changes in polymers of diethyl . . . ", p. 15, and J. Polym. Sci., Part a-1 1971 9(9), 2481–91.
Chemical Abstracts, vol. 93, No. 23, Dec. 8, 1980, Columbus Ohio, U.S.; Abstract No. 22041E, J. Sinnreich; "Chemistry of succinylsuccinic acid derivatives . . . ", p. 500, and Synthesis 1980, (7), 58–80.

*Primary Examiner*—Ellen McAvoy
*Attorney, Agent, or Firm*—Millen, White, Zelano & Branigan

[57] ABSTRACT

Polynitrogen compound having two terminal cycles of the imide type, its preparation by conventional organic chemistry methods and its use as an additive for engine fuel. This compound complies with the general formula (I):

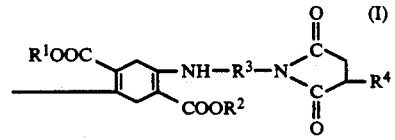

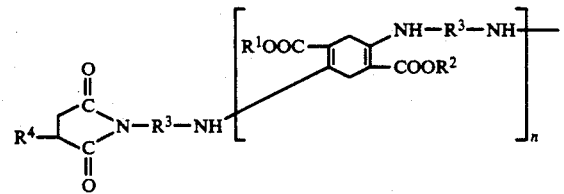

in which $R^1$, $R^2$, $R^3$, and $R^4$ are as set forth in the specification.

14 Claims, No Drawings

POLYNITROGEN COMPOUND HAVING TWO TERMINAL CYCLES OF THE IMIDE TYPE, THEIR PREPARATIONS AND USES

The present invention relates to polynitrogen compounds having two terminal cycles of the imide type, their preparation processes and uses. In their formulas, these compounds normally have at least two nitrogen atoms in addition to the nitrogen atoms of the imide cycles and comply with the following general formula (I):

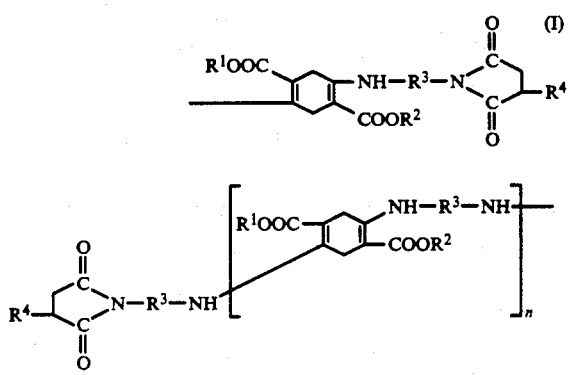

in which $R^1$ and $R^2$, which can be the same or different, in each case represent a hydrocarbon group having 1 to 120 carbon atoms or a group of formula $R^5-(-O-R^6-)_a-(-OR^7-)_b-$ in which $R^6$ and $R^7$, which can be the same or different, each represent a divalent hydrocarbon group having 2 to 6 carbon atoms, $R^5$ represents a monovalent hydrocarbon group having 1 to 60 carbon atoms, a is zero or an integer from 1 to 100 and b is an integer from 1 to 100, $R^3$ is a divalent hydrocarbon group having 2 to 60 carbon atoms or a divalent group of formula

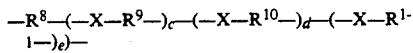

in which X is chosen from among the —O— and —NR$^{12}$— groups, $R^{12}$ representing a hydrogen atom or a hydrocarbon group having 1 to 6 carbon atoms, $R^8$, $R^9$, $R^{10}$ and $R^{11}$, which can be the same or different, each represents a divalent hydrocarbon group having 2 to 6 carbon atoms, c is an integer from 1 to 120, d and e, which can be the same or different, are in each case zero or an integer from 1 to 120 and the sum c+d+e is an integer from 1 to 120, $R^4$ is a hydrogen atom or a hydrocarbon group having 1 to 200 carbon atoms and n is a number from 0 to 20.

In the general formula (I), $R^1$ and $R^2$, which can be the same or different, usually represent in each case a saturated or unsaturated, straight or branched chain aliphatic group having 1 to 60 carbon atoms and e.g. a straight or branched-chain alkyl group having 1 to 30 carbon atoms or a group of formula $R^5-(-O-R^6-)_a-(-OR^7-)_b-$, in which $R^6$ and $R^7$, can be the same or different, usually each represents a saturated or unsaturated, straight or branched-chain, divalent aliphatic group having 2 to 4 carbon atoms and e.g. a straight or branched-chain, alkylene group having 2 to 4 carbon atoms, such as e.g. an ethylene, trimethylene, propylene, tetramethylene and isobutylene group, $R^5$ usually represents a saturated or unsaturated, straight or branched-chain, monovalent aliphatic group having 1 to 20 carbon atoms and e.g. a straight or branched-chain alkyl group having 1 to 20 carbon atoms, a is usually zero or an integer from 1 to 50 and b is usually an integer from 1 to 50, or preferably a is zero or an integer from 1 to 25 and b is preferably an integer from 1 to 25, $R^3$ is usually a saturated or unsaturated, straight or branched-chain, divalent aliphatic group having 2 to 20 carbon atoms, such as e.g. a straight or branched-chain alkylene group having 2 to 20 carbon atoms or a divalent group of formula $-R^8-(-X-R^9-)_c-(-X-R^{10}-)_d-(-X-R^{11}-)_e-$ in which X is chosen from among the groups —O— and —NH—, $R^8$, $R^9$ $R^{10}$ and $R^{11}$, which can be the same or different, in each case represent a saturated or unsaturated, straight or branched-chain, divalent aliphatic group having 2 to 4 carbon atoms, c is an integer from 1 to 60, d and e, which can be the same or different, are in each case zero or an integer from 1 to 60 and the sum c+d+e is an integer from 1 to 60, $R^4$ is usually a saturated or unsaturated, straight or branched-chain, monovalent aliphatic group and preferably a straight or branched-chain alkenyl group, or a group forming with the methylene carbon of the imide cycle, a saturated or unsaturated and preferably unsaturated cycle, which may or may not be bridged, having 5 to 10 carbon atoms and preferably 6 to 8 carbon atoms, said group $R^4$ having 6 to 150 and preferably 6 to 100 and most frequently 12 to 60 carbon atoms and n is usually a number from 0 to 10 and preferably 0 to 5.

The polynitrogen compounds according to the invention can more particularly be used as multifunctional additives for engine fuel. Among these compounds and within the framework of their use as additives for engine fuel, most frequently use is made of those in which the group $R^4$ comprises at least 6 and preferably at least 12 carbon atoms. The addition of a minor proportion of these compounds to an engine fuel in particular makes it possible to limit the fouling of the different parts of the engine and therefore increase the driving pleasure by limiting and/or delaying the appearance of unstable slowing or throttling down and misfiring in the case of controlled ignition engines.

The present invention also relates to compositions incorporating, by weight, a major proportion of an engine fuel and a minor proportion, adequate for modifying at least one of its properties, of at least one compound according to the invention as described hereinbefore or prepared according to one of the methods described hereinafter. These compositions usually incorporate 10 to 10,000 and preferably 50 to 5,000 ppm by weight of at least one compound according to the invention as described hereinbefore or prepared according to one of the methods described hereinafter. In the case of controlled ignition engines, the use of compounds according to the invention in particular makes it possible to limit the value of the increase in the octane requirement of the engine during its operation. This increase is usually referred to by the term Octane Requirement Increase or ORI. In the case of diesel engines, the use of compound according to the invention more particularly makes it possible to limit the emission of solid particles and smoke. As examples of fuels which can contain at least one composition according to the present invention, reference is made to petrols such as those defined by ASTM Standard D-439, gas oils or diesel fuels, such as those defined e.g. by ASTM Standard D-975. These fuels can also contain other additives, such as e.g., particularly in the case of the fuels used for controlled ignition engines, antifouling additives such as lead compounds (e.g. tetraethyl lead), ethers such as methyl tert. butyl ether or methyl tert. amyl ether or a mixture of methanol and tert. butyl alcohol, antiicing additives, anticorrosion additives and additives more specifically of the detergent type. Most frequently the compositions according to the invention are used in combination with a mineral or synthetic oil.

The polynitrogen compounds according to the invention can be produced by all known methods. As non-limitative examples of methods making it possible to prepare the compounds in accordance with the aforementioned general formula (I), reference will be made in an illustrative manner hereinafter to the two following methods.

According to the first preparation method, the compounds of general formula (I) can be obtained by a process having the following stages:

a) reaction takes place in an inert, organic solvent at a temperature of approximately 60° C. to approximately 160° C. of at least one compound according to general formula (III)

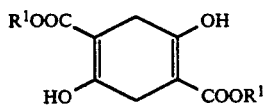

in which $R^1$ and $R^2$ have the meanings given hereinbefore, with at least one alpha-omega biprimary diamine of general formula $NH_2-R^3-NH_2$, in a diamine: compound of general formula (III) molar ratio of approximately 1.1:1 to approximately 10:1, preferably approximately 1.2:1 to approximately 5:1 and e.g. 2:1, so as to form the compound of general formula (II)

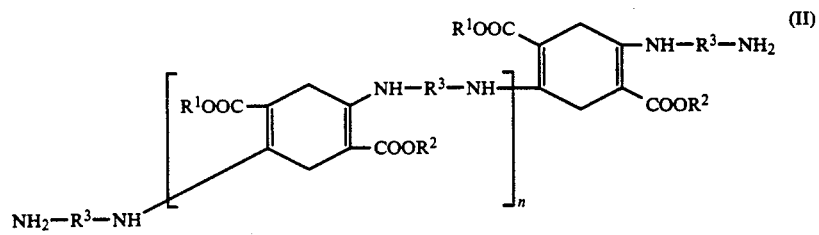

in which $R^1$, $R^2$ and $R^3$ have the meanings given hereinbefore and b) the compound of general formula (II) obtained in stage a) is reacted with an acid or a derivative of a vicinal dicarboxylic acid, at a temperature of approximately 30° C. to approximately 160° C. under conditions appropriate for the formation of imide cycles and the elimination of the volatile products formed, the acid or acid derivative quantity used being approximately at least 2 moles per mole of compound of general formula (II) reacted and optionally isolation takes place in the conventional manner of the compound of general formula (I) formed.

The succinosuccinates used most frequently are commercial compounds or can easily be obtained by conventional synthesis methods. These esters can e.g. be obtained by transesterification starting with dimethyl succinosuccinate (DMSS). As non-limitative examples of these esters, reference is made to esters derived from methanol, ethanol, propanols, butanols, long-chain, primary or secondary alcohols, such as 2-ethyl hexanol, alkylic monoethers of glycol or polyalkylene glycols such as alkyl polypropylene glycol monoethers, polyethylene glycol alkyl monoethers and ethylene glycol and polypropylene alkyl monoethers. The alkyl group of these products usually contains at least 5 carbon atoms and it is usually straight-chained. Examples of the alkyl group are n-pentyl and n-heptyl groups. These oxyalkyl products are commercial products sold by Shell under the generic name OXYLUBE or by ICI. These compounds normally have a molecular weight of approximately 500 to approximately 2500 and usually approximately 600 to approximately 2000. As examples of these compounds reference can be made to those sold by ICI which have a block structure of type $R^5-O-+q$ (propylene oxide)+p (ethylene oxide), in which $R^5$ represents an alkyl group having 1 to 20 carbon atoms, q is the propylene oxide unit number and p the ethylene oxide unit number.

The alpha-omega biprimary diamines conventionally used are well known in the art. Reference can be made as specific, non-limitative compounds to ethylene diamine, propylene diamine, diethylene triamine, dipropylene triamine, triethylene tetramine, tripropylene tetramine, tetraethylene pentamine, tetrapropylene pentamine, hexamethylene diamine, di-(trimethylene)-triamine, dimethyl-2,2-propane-1,3-diamine, N,N'-bis(3-amino propyl)-ethylene diamine, (2-amino ethyl)-3-amino propyl amine and trimethyl hexamethylene diamines, for the case of amines not containing oxygen atoms in their formula. In the case of amines containing oxygen atoms in their formula, reference can be made to polyamines of formula $$NH_2-R^8-(-O-R^9-)_c-(-O-R^{10}-)_d-(-OR^{11}-)_e-NH_2$$

in which preferably $R^8$, $R^9$, $R^{10}$ and $R^{11}$, which can be the same or different, in each case represent an alkylidene group having 2 to 4 carbon atoms, e.g. ethylidene, propylidene, isopropylidene, butylidene or isobutylidene, preferably c is an integer from 1 to 60 and d and e are equal to zero, or c is an integer from 1 to 59, e is zero or an integer such that the sum c+e is 1 to 59 and d is an integer from 1 to 50, with in each case the sum c+d+e equal to an integer from 1 to 60.

As specific diamines, reference can be made to those complying with the formulas:

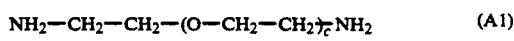

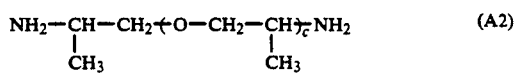

in which c is 2,3,5,6 or approximately 33, or to the formula

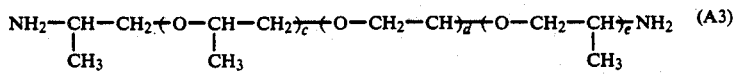

in which d is approximately equal to 8,9,15,16 or 40 and c+e is approximately 2 or 3.

These products are in particular marketed by Texaco Chemicals under the name Jeffamine EDR 148 for the product of formula (A1) in which c=2, Jeffamine D-230 for a product of formula (A2) having a number average molecular weight of 230, Jeffamine D-400 for a product of formula (A2) with a number average molecular weight of 400, Jeffamine D-2000 for a product of formula (A2) having a number average molecular weight of 2000, Jeffamine ED-600 for a product of formula (A3) of number average molecular weight 600, Jeffamine ED-900 for a product of formula (A3) of number average molecular weight 900 and Jeffamine ED-2001 for a product of formula (A3) with a number average molecular weight of 2000.

The acid or acid derivative normally used within the scope of the present invention is a succinic compound or an alkyl succinic or alkenyl succinic compound and preferably a succinic anhydride. It is also possible to use a phthalic derivative, preferably phthalic anhydride or a phthalic anhydride having an alkyl group on one of the carbon atoms of the nucleus. As examples of compounds of the succinic type, reference can be made to succinic anhydride, methyl succinic anhydride, often known as citraconic anhydride, and alkyl succinic or alkenyl succinic anhydrides normally having a number average molecular weight of approximately 200 to 3000 and preferably 500 to 2000, most frequently 700 to 1500. These succinic derivatives are well known in the art and are e.g. obtained by the action of at least one alpha olefin or a chlorinated hydrocarbon on the maleic anhydride or acid. The alpha olefin or chlorinated hydrocarbon used in this synthesis can be straight or branched-chain and normally have 10 to 150 carbon atoms, preferably 15 to 80 carbon atoms and most frequently 20 to 75 carbon atoms in their molecule. This olefin can also be an oligomer, e.g. a dimer, trimer or tetramer, or a polymer of a lower olefin, e.g. having 2 to 10 carbon atoms, such as ethylene, propylene, n-1-butene, isobutene, n-1-hexene, n-1-octene, 2-methyl-1-heptene or 2-methyl-5-propyl-1-hexene. It is possible to use mixtures of olefins or mixtures of chlorinated hydrocarbons.

As examples of succinic anhydrides, reference can be made to n-octadecenyl succinic anhydride, dodecenyl succinic anhydride and polyisobutenyl succinic anhydrides, often called PIBSA, having a number average molecular weight as defined hereinbefore.

According to the second preparation method, the compounds of general formula (I), particularly those in which n is equal to zero, can be obtained by a process having the following stages:
a) at least one alpha-omega biprimary diamine of general formula NH$_2$—R$^3$—NH$_2$ is reacted with an acid or a derivative of a vicinal dicarboxylic acid, at a temperature of approximately 30° C. to approximately 160° C. under conditions suitable for the formation of imide cycles and for the elimination of the volatile products formed, the acid or acid derivative quantity used being approximately 1 mole per mole of diamine, so as to form the compound of general formula (IV)

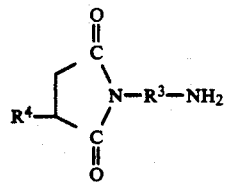

in which R$^3$ and R$^4$ have the meanings given hereinbefore and
b) the compound of general formula (IV) obtained in stage a) is reacted with the compound of general formula (III), in a molar ratio of approximately 2 moles of compound of general formula (IV) per mole of compound of general formula (III), under conditions suitable for the formation of a compound of general formula (I), in which n=0.

Within the scope of the present invention it is possible to use, for the synthesis of products of formulas (I), (II) or (IV), one or more biprimary diamines.

The following examples illustrate the invention without limiting its scope.

EXAMPLE 1 a) First stage

Into a double-envelope, 2 liter reactor equipped with a stirring system, a dip tube permitting an introduction of argon, a thermometer and a condenser are introduced, accompanied by stirring, 784.3 grammes (g) (3.44 moles) of dimethyl succinosuccinate (DMSS) and 984.1 g (7.57 moles) of 2-ethyl hexanol. The temperature is raised to 135° C., followed by the introduction of 11.6 g (3.4×10$^{-2}$ mole) of butyl titanate Ti-(OC$_4$H$_9$)$_4$ and the temperature is then raised to 145° C., whilst maintaining stirring. The temperature of 145° C., accompanied by stirring, is maintained for 90 minutes. A first methanol fraction is collected at atmospheric pressure, followed by the progressive reduction of the pressure with the aid of a water jet pump to a value of 27 kilopascals (KPa) and, after condensation, collection takes place (the flask temperature being maintained at 145° C.), of 220.6 g of an alcoholic phase. Gas chromatographic analysis shows that the thus recovered alcoholic phase contains methanol, 2-ethyl hexanol and butanol. The total recovered methanol quantity corresponds to the expected quantity. The reactor contains 1556 g of products which, on the basis of a gel permeation chromatographic analysis, contain 89.4% of 2-diethyl hexyl succinosuccinate, i.e. 1391 g (3.28 moles), which corresponds to a 95% DMSS molar conversion. By distillation under a partial pressure of 270 Pa and at a temperature of 120° C. the residual alcohols are eliminated. The product obtained is dissolved in xylene with a weight ratio of 1:1. The thus obtained solution is called solution 1.

b) Second stage

Into a double-envelope, 2 liter reactor equipped with a stirring system, a pouring funnel, a thermometer and a Dean-Stark separator are introduced 296.8 g of solution 1 (0.35 mole of succinosuccinic acid diester and 2-ethyl hexanol). At ambient temperature and accompanied by stirring, dropwise addition takes place of 560 g of a solution in xylene (xylene:product weight ratio 1:1) of a polyoxypropylene diamine of molecular weight 400 (product sold by Texaco under the name Jeffamine D400), i.e. 0.7 mole of amine. The temperature is progressively raised to 120° C. and collection takes place of 12.5 milliliters (ml) of water, i.e. 99.2% of the theoretical quantity for the formation of a product of formula (II) (2 moles of water per mole of ester). 791 g of a solution called solution 2 is recovered in the reactor. The product obtained is characterized by conventional analytical methods. The infrared spectrum shows intense bands at 1663, 1603 and 1240 cm$^{-1}$, which can be attributed to the ester functions and to the enamine double bond. The structure was confirmed by nuclear magnetic resonance. The number average molecular weight of the product, measured by tonometry, is 2036.

c) Third stage

Into a reactor identical to that used in the second stage are introduced 210 g of solution 2, i.e. 0.0884 mole of product of formula (II). At ambient temperature and accompanied by stirring, dropwise introduction takes place of 295.2 g of a solution (1:1 by weight) in xylene of polyisobutene succinic anhydride with 0.12 anhydride function per 100 g, i.e. 0.177 mole. The temperature is progressively raised to the reflux temperature of the xylene (140° C.). After heating for 2 hours 3.17 ml of water are collected, i.e. approximately the theoretical quantity corresponding to the formation of imide cycles. Recovery takes place of 497 g of a 50% by weight solution of product in xylene. This solution is called additive 1 and was analysed after evaporating the solvent. Its number average molecular weight, measured by tonometry, is 3500. The infrared spectrum shows the following characteristic bands: 1610 cm$^{-1}$ attributable to the enamine double bond, 1660 cm$^{-1}$ attributable to the carbonyl bond of the sulpho succinate and the characteristic doublet of the aliphatic succinimides at 1710 and 1770 cm$^{-1}$.

EXAMPLE 2 a) First stage

Into a double-envelope, 2 liter reactor equipped with a stirring system, a pouring funnel, a thermometer and a Dean-Stark separator are introduced 160 g of a 50% by weight polyoxypropylene-diamine solution in xylene having a molecular weight of 400 (product sold by Texaco under the name Jeffamine D-400), i.e. 0.2 mole of amine. At ambient temperature and accompanied by stirring, dropwise introduction takes place into the xylene of 333 g of a 50% by weight solution of polyisobutene succinic anhydride with 0.12 anhydride function per 100 g, i.e. 0.2 mole. The temperature is then progressively raised to the reflux temperature of the xylene (140° C.). After reacting for 2 hours at 140° C., 3.6 g of water were collected corresponding to the theoretical quantity for the formation of a succinimide cycle. In the reactor recovery took place of 487 g of a solution called solution 3. The product obtained is characterized by conventional analytical methods.

b) Second stage

Into a reactor identical to that used in the first stage are introduced 84.8 g of solution 1 prepared during the first stage of Example 1, i.e. 0.1 mole of succino succinic acid diester and 2-ethyl hexanol. At ambient temperature and accompanied by stirring dropwise addition takes place of 487 g of solution 3 obtained in the first stage. The temperature is progressively raised to 120° C. and collection takes place of 3.5 ml of water, i.e. 97% of the theoretical quantity for the formation of a product of formula (I) (2 moles of water per mole of diester), in which n=0. There is a recovery of 568 g of a 50% by weight product solution in xylene. This solution is called additive 2, which was analysed after evaporating the solvent. Its number average molecular weight, measured by tonometry, is 2800. The infrared spectrum shows the following characteristic bands: 1610 cm$^{-1}$ attributable to the enamine double bond, 1660 cm$^{-1}$ attributable to the carbonyl bond of the succinosuccinate and the characteristic doublet of aliphatic succinimides at 1710 and 1770 cm$^{-1}$.

EXAMPLE 3

The procedure described in Example 1 is repeated using in the second stage a polyoxypropylene diamine of molecular weight 2000 (product sold by Texaco under the name Jeffamine D-2000). Use was made of 106 g (0.125 mole) of solution 1 and 1000 g (0.25 mole) of a 50% by weight Jeffamine D-2000 solution in xylene. Reflux is maintained for the time necessary for collecting the theoretical water quantity for the formation of a product of formula (II). This gives a solution 4, from which is removed 281.2 g (0.0415 mole of product of formula (II)) for the third stage, where use is made of 138.4 g (0.083 mole of anhydride) of the 50% by weight solution in xylene of the polyisobutene succinic anhydride with 0.12 anhydride function for 100 g. A 50% by weight product solution in xylene is recovered and the solution is called additive 3.

EXAMPLE 4

The procedure of Example 3 is repeated using in the third stage a polyisobutene succinic anhydride having 0.074 anhydride function per 100 g. Use is made of 240 g of solution 4 and 191.6 g (0.0708 mole) of the 50% by weight solution of said polyisobutene succinic anhydride. This gives a 50% by weight product solution in xylene. This solution is called additive 4 and was analysed after evaporating the solvent. Its number average molecular weight, measured by tonometry, is 7200.

EXAMPLE 5

The procedure of Example 3 is repeated, using in the third stage tetrapropenyl succinic anhydride (ATPS). Use is made of 313.7 g (0.0463 mole of product) of solution 4 and 49.2 g of the 50% by weight solution in xylene of ATPS. This gives a 50% by weight product solution in xylene and the solution is called additive 5.

EXAMPLE 6

The procedure described in Example 1 is repeated, using in the first stage, instead of 2-ethyl hexanol, a polyoxypropylated and ethoxylated monoalcohol (sold by ICI) having 70% primary alcohol function and a molecular weight of 1097. Use is made of 182.4 g (0.8 mole) of DMSS and 2512 g (2.29 moles) of polyoxyalkylated alcohol (i.e. a 30% excess). After diluting in xylene, a 50% by weight product solution, called solution 5 is obtained. An aliquot quantity of solution 5 corresponding to 0.3 mole of the starting DMSS is sampled. This aliquot quantity of solution 5 is reacted under the conditions described for the second stage in Example 1 with 440 g of a 50% by weight solution in xylene of Jeffamine D-400, i.e. 0.6 mole. The water quantity collected corresponds to the expected theoretical quantity for the formation of a product of formula (II) (2 moles of water per mole of diester) This gives 2195 g of a solution called solution 6. Part of said solution 6 is removed corresponding to 0.0425 mole of DMSS, i.e. 0.085 primary amine function, which is reacted under conditions described in connection with stage 3 of Example 1, with 141.7 g of a 50% by weight solution in xylene of polyisobutene succinic anhydride with 0.12 function per 100 g, i.e. 0.085 mole. Recovery takes place of a 50% by weight product solution in xylene and this solution is called additive 6.

EXAMPLE 7

The procedure described in Example 6 is repeated, using in the third stage a polyisobutene succinic anhydride with 0.074 anhydride function per 100 g. The same quantity of solution 6 is used as in Example 6 (i.e. 0.085 primary amine function) and 230 g of a 50% by weight solution in xylene of anhydride, i.e. 0.085 mole. A 50% by weight product solution in xylene is recovered and is called additive 7.

EXAMPLE 8

The procedure described in Example 2 is repeated using, in the first stage and in the form of a 50% by weight solution in xylene, 0.2 mole of tetraethylene pentamine and 0.2 mole of polyisobutene succinic anhydride with 0.074 function per 100 g. Reaction takes place in the second stage of 0.1 mole of DMSS with 0.29 mole of polyoxyalkylated alcohol used in Example 6 and under the conditions described hereinbefore for the transesterification. The third stage is performed under the same conditions as described in conjunction with Example 2. This gives a solution in xylene, which is adjusted to 50% by weight of product and which is called additive 8.

EXAMPLE 9

The procedure described in Example 8 is repeated replacing the tetraethylene pentamine by hexamethylene diamine. This gives a solution in xylene which, adjusted to 50% by weight of product, constitutes additive 9.

The additives prepared in Examples 3 to 9 all have, in infrared spectroscopy, the same characteristic bands as the additives obtained in Examples 1 and 2.

EXAMPLE 10

A series of tests is performed for evaluating the properties of limiting the octane requirement increase of an engine supplied by a fuel only, a fuel containing one of the additives according to the invention and also a conventional detergent additive (C) and a fuel containing additive C, but not the anti-ORI additive. The fuel used is a leadfree fuel containing by volume 26% aromatics, 6.3% olefins and 67.7% saturated compounds (paraffins and naphthenes).

The anti-ORI additives according to the invention were added to the fuel so as to have a concentration by weight of 100 ppm. The tests were performed on an engine test stand equipped with a F 2 N Renault engine with a stroke volume of 1721 cm$^3$ and a compression ratio of 9.5. These tests were carried out following the modified Renault 22700 procedure using a water temperature on leaving the cylinder head of 95° C.±2° C. and an oil temperature of 140° C. The test cycle lasts 12 hours (h) and consists of 3 h at of slowing down empty, 4 h at 2500 rpm at half full load, 3 h at 3500 rpm empty and 4 h at 2500 rpm at half the full load.

The advance values corresponding to the appearance of chatter and expressed in crankshaft degrees and often known as the Knock Limit Spark Advance or KLSA are determined once at 0 and 150 hours under different engine speeds. The results obtained are expressed as KLSA variations at 150 hours for four different engine speeds, i.e. 2000, 2900, 3600 and 4100 rpm. These results are given in the following table 1. The overall weight of the deposits on the induction valve was also measured and the results are given in table 1. These results show that the additives according to the invention give lower KLSA variations, limit the increase of the octane requirement of the engine and delay the appearance of unstable slowing down. The weight of the deposits on the intake valves is significantly reduced compared with what is obtained with the fuel only or with the fuel containing detergent additive C.

TABLE 1

| Δ KLSA at | Fuel only | Fuel + additive C without anti-ORI | Fuel + additive C + additive 4 | Fuel + additive C + additive 6 |
|---|---|---|---|---|
| 2000 rpm | 5 | 8 | 3 | 4 |
| 2900 rpm | 4 | 10 | 3 | 3 |
| 3600 rpm | 4 | 16 | 2 | 3 |
| 4100 rpm | 7 | 15 | 6 | 6 |
| deposits in g. | 2.01 | 1.20 | 0.91 | 1.18 |

EXAMPLE 11

Tests were carried out for evaluating the anti-smoke properties of additives according to the invention in a diesel fuel, which had the following characteristics:

| Filtrability limit temperature | −3° C. |
|---|---|
| Initial distillation point | 162° C. |
| 95% distillation point | 366° C. |
| Density at 15° C. | 0.8331 |
| Calculated cetane number | 50.4 |

The additive quantity is added to the fuel so as to obtain a concentration, by weight of active matter in the additive-containing fuel, of 100 ppm.

The tests were carried out on the Renault F 8 Q engine in accordance with the procedure described hereinafter. After starting, the engine was allowed to heat and the cooling water temperature was regulated to 85° C. The engine speed was fixed at 2500 rpm under half-loads for approximately 15 minutes before measuring the smoke point. This measurement was carried out according to the Bosch method. Table 2 gives the results obtained with the non-additive-containing fuel and with the fuel containing additive 4.

TABLE 2

| Fuel | Bosch small point |
|---|---|
| Fuel only | 2.3 |
| Fuel + additive 4 | 0.8 |

These results show that the additive 4 prepared in Example 4 makes it possible to significantly reduce the smoke level emitted in the exhaust of a diesel engine.

We claim:

1. A polynitrogen compound having two terminal cycles of the imide type and complying with the general formula (I):

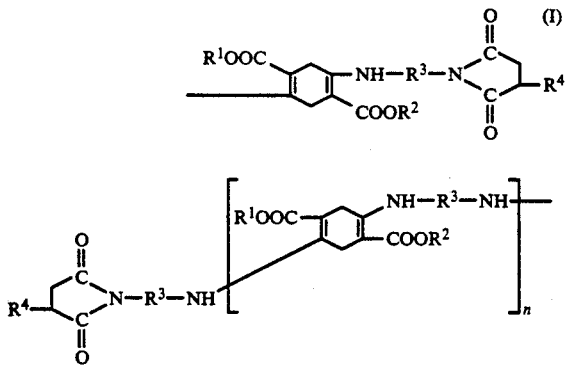

in which $R^1$ and $R^2$, which can be the same or different, in each case represent a hydrocarbon group having 1 to 120 carbon atoms or a group of formula $R^5-(-O-R^6-)_a-(OR^7-)_b-$ in which $R^6$ and $R^7$, which can be the same or different, each represent a divalent hydrocarbon group having 2 to 6 carbon atoms, $R^5$ represents a monovalent hydrocarbon group having 1 to 60 carbon atoms, a is zero or an integer from 1 to 100 and b is an integer from 1 to 100, $R^3$ is a divalent hydrocarbon group having 2 to 60 carbon atoms or a divalent group of formula

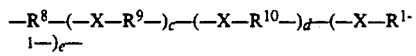

in which X is chosen from among the —O— and —NR$^{12}$— groups, $R^{12}$ representing a hydrogen atom or a hydrocarbon group having 1 to 6 carbon atoms, $R^8$, $R^9$, $R^{10}$ and $R^{11}$, which can be the same or different, each represents a divalent hydrocarbon group having 2 to 6 carbon atoms, c is an integer from 1 to 120, d and e, which can be the same or different, are in each case zero or an integer from 1 to 120 and the sum c+d+e is an integer from 1 to 120, $R^4$ is a hydrogen atom or a hydrocarbon group having 1 to 200 carbon atoms and n is a number from 0 to 20.

2. A compound according to general formula (I) of claim 1, in which $R^1$ and $R^2$, which can be the same or different, in each case represent a saturated or unsaturated, straight or branched-chain, aliphatic group having 1 to 60 carbon atoms or a group of formula $R^5-(-O-R^6-)_a-(-O-R^7-)_b-$, in which $R^6$ and $R^7$, which can be the same or different, each represent a saturated or unsaturated, straight or branched-chain, aliphatic group with 2 to 4 carbon atoms, $R^5$ represents a saturated or unsaturated, straight or branched-chain, monovalent aliphatic group with 1 to 20 carbon atoms, a is zero or an integer from 1 to 50 and b is an integer from 1 to 50, $R^3$ is a saturated or unsaturated, straight or branched-chain, divalent aliphatic group having 2 to 20 carbon atoms or a divalent group of formula

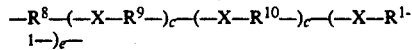

in which X is chosen from among the —O— and —NH— groups, $R^8$, $R^9$, $R^{10}$ and $R^{11}$, which can be the same or different, in each case represent a saturated or unsaturated, straight or branched-chain, divalent aliphatic group having 2 to 4 carbon atoms, c is an integer from 1 to 60, d and e, which can be the same or different, are in each case zero or an integer from 1 to 60 and the sum c+d+e is an integer from 1 to 60, $R^4$ is a saturated or unsaturated, straight or branched-chain, monovalent aliphatic group or a group forming with the methylene carbon of the imide cycle, a saturated or unsaturated, bridged or unbridged cycle, having 5 to 10 carbon atoms, said group $R^4$ having 6 to 150 carbon atoms and n is a number from 0 to 10.

3. A compound of general formula (I) according to claim 1, wherein $R^1$ and $R^2$, which can be the same or different, in each case represent a straight or branched-chain alkyl group with 1 to 30 carbon atoms or a group of formula $R^5-(-O-R^6-)_a-(-O-R^7-)_b-$, in which $R^6$ and $R^7$, which can be the same or different, in each case represent a straight or branched-chain alkylene group having 2 to 4 carbon atoms, $R^5$ is a straight or branched-chain alkyl group with 1 to 20 carbon atoms, a is zero or an integer from 1 to 25 and b is an integer from 1 to 25, $R^3$ is a straight or branched-chain alkylene group having 2 to 20 carbon atoms, $R^4$ is a straight or branched-chain alkenyl group or a group forming with the methylene carbon of the imide cycle an unsaturated, bridged or unbridged cycle having 6 to 8 carbon atoms, said group $R^4$ having 6 to 100 carbon atoms and n is a number from 0 to 5.

4. A compound of general formula (I) according to claim 1, wherein $R^1$ and $R^2$, which can be same or different, in each case represent a straight or branched-chain alkyl group having 1 to 30 carbon atoms or a group of formula $R^5-(-O-R^6-)_a-(-O-R^7-)_b-$ in which $R^6$ and $R^7$, which can be the same or different, each represent a straight or branched-chain alkyl group having 2 to 4 carbon atoms, $R^5$ is a straight or branched-chain alkyl group having 1 to 20 carbon atoms, a is zero or an integer from 1 to 25 and b is an integer from 1 to 25, $R^3$ is a divalent group of formula

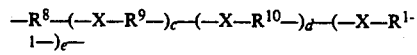

in which X is chosen from among the groups —O— and —NH—, $R^8$, $R^9$, $R^{10}$ and $R^{11}$, which can be the same or different, each represent a saturated or unsaturated, straight or branched-chain, aliphatic group having 2 to 4 carbon atoms, c is an integer from 1 to 60, d and e, which can be the same or different, are in each case zero or an integer from 1 to 60 and the sum c+d+e is an integer from 1 to 60, $R^4$ is a straight or branched-chain alkenyl group or a group forming with the methylene carbon of the imide cycle, an unsaturated, bridged or unbridged cycle having 6 to 8 carbon atoms, said group $R^4$ having 6 to 100 carbon atoms and n is an integer from 0 to 5.

5. A compound of general formula (I) according to claim 1, wherein $R^1$ and $R^2$, which can be the same or different, each represent a saturated or unsaturated, straight or branched-chain aliphatic group with 1 to 60 carbon atoms, $R^3$ is a divalent group of formula —$R^8-(-X-R^9-)_c-(-X-R^{10}-)_d-(-X-R^{11}-)_e-$ in which X is chosen from among the groups —O— and —NH—, $R^8$, $R^9$, $R^{10}$ and $R^{11}$, which can be the same or different, each represent a saturated or unsaturated, straight or branched-chain, aliphatic group having 2 to 4 carbon atoms, c is an integer from 1 to 60, d and e, which can be the same or different, are in each case zero or an integer from 1 to 60 and the sum c+d+e is an integer from 1 to 60, $R^4$ is a straight or branched-chain alkenyl group or a group forming with the methylene carbon of the imide cycle an unsaturated, bridged or unbridged cycle having 6 to 8 carbon atoms, said group $R^4$ having 6 to 100 carbon atoms and n is a number from 0 to 5.

6. A compound of general formula (I) according to claim 1, wherein $R^1$ and $R^2$, which can be the same or different, each represent a group of formula

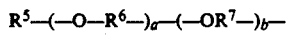

$R^5-(-O-R^6-)_a-(-OR^7-)_b-$ in which $R^6$ and $R^7$, which can be the same or different, each represent a saturated or unsaturated, straight or branched-chain, divalent aliphatic group having 2 to 4 carbon atoms, $R^5$ represents a saturated or unsaturated, straight or branched-chain, aliphatic group with 1 to 20 carbon atoms, $R^3$ is a divalent group of formula $-R^8-(-X-R^9-)_c-(-X-R^{10}-)_d-(-X-R^{11}-)_e-$, in which X is chosen from among the groups $-O-$ and $-NH-$, $R^8$, $R^9$, $R^{10}$ and $R^{11}$, which can be the same or different, each represent a saturated or unsaturated, straight or branched-chain aliphatic group having 2 to 4 carbon atoms, c is an integer from 1 to 60, d and e, which can be the same or different, are in each case zero or an integer from 1 to 60 and the sum c+d+e is an integer from 1 to 60, $R^4$ is a straight or branched-chain alkenyl group or a group forming with the methylene carbon of the imide cycle a bridged or unbridged, unsaturated cycle having 6 to 8 carbon atoms, said group $R^4$ having 6 to 100 carbon atoms and n is a number from 0 to 5.

7. A compound of general formula (I) according to claim 4, wherein $R^3$ is a divalent group of formula $-R^8-(-X-R^9-)_c-(-X-R^{10}-)_d-(-X-R^{11}-)_e-$, in which X is the group $-O-$, $R^8$, $R^9$, $R^{10}$ and $R^{11}$, which can be the same or different, each represent a saturated or unsaturated, straight or branched-chain, aliphatic group having 2 to 4 carbon atoms, c is an integer from 1 to 60, d and e, which can be the same or different, are in each case zero or an integer from 1 to 60 and the sum c+d+e is an integer from 1 to 60.

8. A compound of general formula (I), according to claim 4, wherein $R^3$ is a divalent group of formula $-R^8-(-X-R^9-)_c-(-X-R^{10}-)_d-(-X-R^{11}-)_e-$, in which X is the group $-NH-$, $R^8$, $R^9$, $R^{10}$ and $R^{11}$, which can be the same or different, each represent a saturated or unsaturated, straight or branched-chain, aliphatic group with 2 to 4 carbon atoms, c, d and e, which can be the same or different, are in each case zero or an integer from 1 to 60.

9. A process for the preparation of a compound according to claim 1, comprising the following stages:
   a) reaction takes place in an inert, organic solvent at a temperature of approximately 60° C. to approximately 160° C. of at least one compound of general formula (III)

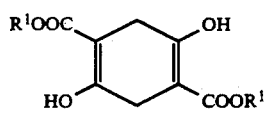

with at least one alpha-omega biprimary diamine of general formula $NH_2-R^3$, $NH_2$, in a diamine: compound of general formula (III) molar ratio of approximately 1.1:1 to approximately 10:1, so as to form the compound of general formula (II)

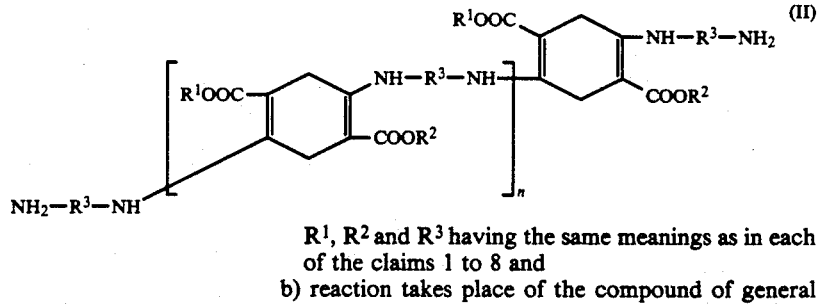

$R^1$, $R^2$ and $R^3$ having the same meanings as in each of the claims 1 to 8 and b) reaction takes place of the compound of general formula (II) obtained in stage a) with an acid or a derivative of a vicinal dicarboxylic acid, at a temperature of approximately 30° C. to approximately 160° C. under the conditions for the formation of imides cycles and the elimination of the volatile products formed, the acid or acid derivative quantity used being approximately at least 2 moles per mole of compound of general formula (II) reacted.

10. A process for the preparation of a compound according to claim 1, characterized in that it comprises the following stages:
   a) reaction takes place of at least one alpha-omega biprimary diamine of general formula $NH_2-R^3-NH_2$, with an acid or a derivative of a vicinal dicarboxylic acid, at a temperature from approximately 30° C. to approximately 160° C. under conditions for the formation of imide cycles and for the elimination of the volatile products formed, the acid or acid derivative quantity used being approximately 1 mole per mole of diamine, so as to form the compound of general formula (IV)

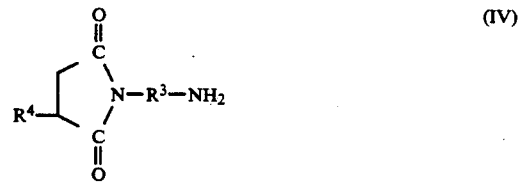

$R^3$ and $R^4$ having the same meanings as in each of the claims 1 to 8 and b) reaction takes place of the compound of general formula (IV) obtained in stage a) with the compound of general formula (III), in a molar ratio of approximately 2 moles of compound of general formula (IV) per mole of compound of general formula (III), under conditions suitable for the formation of a compound of general formula (I), in which n=0.

11. A compound according to claim 1.

12. A composition incorporating by weight a major proportion of an engine fuel and a minor proportion, adequate for modifying at least one of its properties, of at least one compound according to claim 1.

13. A composition according to claim 12 incorporating 10 to 10,000 ppm by weight of said at least one compound.

14. A composition according to claim 12 incorporating 50 to 5,000 ppm by weight of said at least one compound.

* * * * *